United States Patent [19]

Pocock

[11] Patent Number: 5,227,290
[45] Date of Patent: Jul. 13, 1993

[54] METHOD FOR CONDUCTING DIAGNOSTIC ASSAYS

[76] Inventor: Douglas A. Pocock, 88 Stockbridge Rd., Scituate, Mass. 02066

[21] Appl. No.: 771,830

[22] Filed: Oct. 7, 1991

Related U.S. Application Data

[63] Continuation of Ser. No. 575,132, Aug. 29, 1990, abandoned.

[51] Int. Cl.$^5$ ............ B01D 35/00; G01N 33/53; C12M 1/12
[52] U.S. Cl. .................... 435/7.1; 435/311; 210/406; 422/101; 422/56; 436/178
[58] Field of Search ............ 422/56, 58, 61, 81, 422/101; 436/174, 177, 178; 435/287, 311, 7.1, 288; 210/323.1, 406

[56] References Cited

U.S. PATENT DOCUMENTS

| | | | |
|---|---|---|---|
| 3,730,352 | 5/1973 | Cohen et al. | 210/406 |
| 4,704,255 | 11/1987 | Jolley | 422/101 |
| 4,777,021 | 11/1988 | Wertz et al. | 436/178 |
| 4,806,487 | 2/1989 | Akers et al. | 436/178 |
| 4,816,415 | 3/1989 | Akers et al. | 436/178 |
| 4,948,561 | 8/1990 | Hinckley | 436/178 |
| 4,965,187 | 9/1990 | Tonelli | 436/177 |
| 4,988,627 | 1/1991 | Smith-Lewis | 436/178 |
| 5,039,493 | 8/1991 | Oprandy | 422/101 |
| 5,141,719 | 8/1992 | Fernwood et al. | 422/101 |

Primary Examiner—Robert J. Warden
Assistant Examiner—T. A. Trembley
Attorney, Agent, or Firm—Lorusso & Loud

[57] ABSTRACT

A diagnostic device for conducting enzymatic and chromogenic assays, the device having a plurality of test conduits therein, individual assay means disposed in each of the conduits, barrier walls extending between adjoining conduits to proximate a bottom wall of the device, to discourage liquid passing through one of the conduits to enter an adjoining conduit, and methods for assembling and using the device.

3 Claims, 2 Drawing Sheets

METHOD FOR CONDUCTING DIAGNOSTIC ASSAYS

This is a continuation of copending application(s) Ser. No. 07/575,132 filed on Aug. 29, 1990 now abandoned.

BACKGROUND OF THE INVENTION

1. Field of the Invention

This invention relates to assay devices and is directed more particularly to methods for using a diagnostic device for conducting enzymatic and chromogenic assays of liquid substances.

2. Description of the Prior Art

Assays are useful for the quantitation of antigen/-hapten, antibody analyte, or analyte occurring on or attached to cells, or other particulate material, contained in liquid samples of body fluids, such as serum, plasma, urine, or saliva, and non-body fluids, such as cell culture media, potable water, and waste water.

A known assay device includes a housing having a number of "wells" therein, which serve as reaction vessels for chemical reactions. A filter membrane is located at the bottom of each well, and beneath the membrane is a waste reservoir. By applying a vacuum, or a reduced pressure, to the waste reservoir, the liquid undergoing test is drawn through the membrane and into the waste reservoir. As the liquid undergoing test is drawn through the membrane, particulates, or the solid phase, of the liquid is deposited on the membrane. The membrane is exposed to the flowing liquid in a limited area, such that the deposited particulates are concentrated. The deposited particulates may be bacteria, cell fragments, or the like.

The membrane may be provided with antigens, haptens, or their antibodies, to react with a target particulate of the liquid to produce a manifestation of a particular combination, the manifestation often taking the form of producing a certain color. Such "chromogenic" assays may be used for simple and quick tests for various bacteria. A small amount, typically no more than one milliliter, of a liquid is dropped into a "well" and caused by a vacuum bias to be drawn through a previously prepared membrane and into a waste reservoir. Particulates in the liquid are retained and concentrated by the membrane and react with the immunoreactant with which the membrane has been previously supplied. Given reactions produce differing colors. For example, a positive indication as to presence in the liquid of a target bacteria may be manifested by a purple color, while a negative indication may be manifested by a white color.

Such devices of the prior art have, on occasion, suffered from "migration" of liquid from one well area to an adjacent well area and, in particular, to a neighboring membrane. U.S. Pat. No. 4,704,255, issued Nov. 3, 1987 in the name of Michael E. Jolley, is illustrative of such devices which typically include a number of wells (96 in the Jolley device), all served by a single membrane and a single waste reservoir. Thus, migration can occur in the membrane itself, and/or in the waste reservoir, from the area of one well to a neighboring well.

It would be beneficial to have available an assay device of the general type above described, but having individual and segregated membrane means for each "well" or test conduit, and individual and segregated waste reservoir means for each of the test conduits.

SUMMARY OF THE INVENTION

It is, therefore, an object of the present invention to provide a diagnostic device for conducting assays on liquid substances, the device having means for discouraging movement of such liquid from one test conduit to another.

A further object of the invention is to provide such a device in which a vacuum constitutes a moving force for the liquid undergoing assay, and to provide a vacuum generating apparatus which is operative in conjunction with the diagnostic device, to provide a diagnostic assembly.

A still further object of the invention is to provide such a diagnostic device having a plurality of conduits therein, and an assay means disposed in each of the conduits, the assay means comprising a membrane assembly.

A still further object of the invention is to provide methods for assembling and using the diagnostic assembly.

With the above and other objects in view, as will hereinafter appear, a feature of the present invention is the provision of a diagnostic device for conducting enzymatic and chromogenic assays, the device comprising a first housing having a plurality of openings in a top surface thereof, wall means defining the openings and depending from the top surface to define conduits extending from the top surface through the first housing, the wall means including barrier walls disposed between each adjoining two conduits, assay means disposed in each of the conduits, the assay means being adapted to permit flow therethrough of a liquid substance undergoing test, the barrier walls extending beyond a bottom plane of the first housing, a second housing comprising a bottom wall and upstanding side walls, the first housing being connected to the second housing, a distal edge of each of the barrier walls being proximate the bottom wall, and means for reducing pressure in the second housing to draw the liquid through the conduit and the assay means and into the second housing, the barrier walls discouraging movement of the liquid from one of the conduits to the assay means of another of the conduits.

In accordance with another feature of the invention, there is provided in the device described immediately above, an absorbent material on the bottom wall of the second housing, the distal edges of the barrier walls being adjacent the absorbent material, whereby to further discourage movement of liquid undergoing assay in one conduit to the assay means of the adjoining conduit.

In accordance with a further feature of the invention, there is provided for use in conjunction with the above-described diagnostic device a vacuum generating apparatus, the apparatus comprising a housing having a trough therein adapted to receive the diagnostic device, a luer extending inwardly of the trough from a wall thereof, the luer being adapted to be aligned with the diagnostic device port, the luer being in communication with a vacuum source means disposed in the apparatus housing, whereby to facilitate generation of a vacuum in the diagnostic device, while leaving exposed the top surface of the diagnostic device to facilitate introduction of the liquid into the conduits.

In accordance with a still further feature of the invention, there is provided an individual assay means for each of the conduits, each of the assay means including a membrane holder assembly comprising a first plate member having a first orifice therethrough, a second plate member having a recess therein and a second orifice in the recess and extending through the second plate member, the first and second orifices being substantially in alignment, the second plate member being adapted to receive and retain membrane means in the recess therein, the first and second plates being adapted to be joined together with the membrane means disposed between the first and second orifices.

In accordance with a still further feature of the invention, there is provided a method for assembling an assay device comprising providing a housing having openings in a top surface thereof, walls depending from the top surface to define conduits through the housing, the walls including a barrier wall between each two of the conduits, the barrier walls extending beyond a bottom plane of the housing, the housing including a reservoir portion comprising a bottom wall and side walls upstanding therefrom, the barrier walls extending into the reservoir portion with distal ends of the barrier walls being proximate the bottom wall to provide a reservoir chamber for each of the conduits, and a membrane assembly holder fixed in each of the conduits, placing a first membrane in a recess formed on a first membrane holder plate having a first orifice therein, the first membrane being placed so as to cover the first orifice, attaching a second membrane holder plate having a second orifice therein to the first membrane holder plate with the first membrane therebetween and covering the second orifice, to form a first membrane assembly, and fixing the first membrane assembly in a first of the conduits and on a first of the membrane assembly holders.

In accordance with still another feature of the invention, there is provided a method for using an assay device, the method including the above method for assembling the device, and further including the steps of depositing a liquid to be tested on the first membrane, providing reduced pressure to the reservoir portion to draw the liquid through the first membrane and into the reservoir portion leaving particulate matter from the liquid on the first membrane for test purposes, and upon completion of testing of the particulate, disposing of the device with the particulates and the liquid therein.

The above and other features of the invention, including various novel details of construction and combinations of parts, will now be more particularly described with reference to the accompanying drawings and pointed out in the claims. It will be understood that the particular methods embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown an illustrative embodiments of the invention, from which its novel features and advantages will be apparent.

In the drawings.

DESCRIPTION OF THE PREFERRED EMBODIMENTS

Figure 1:
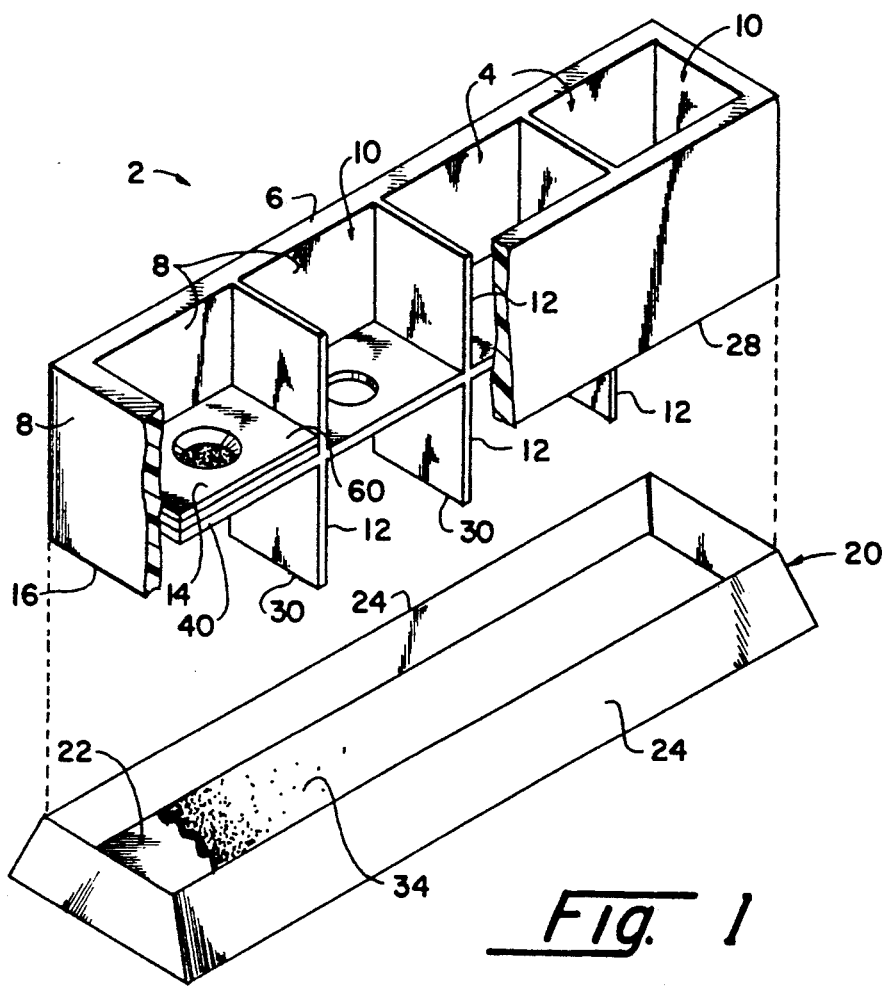
FIG. 1 is an exploded perspective view of first and second housing components of one form of diagnostic device, illustrative of a embodiment of the invention.
Figure 2:
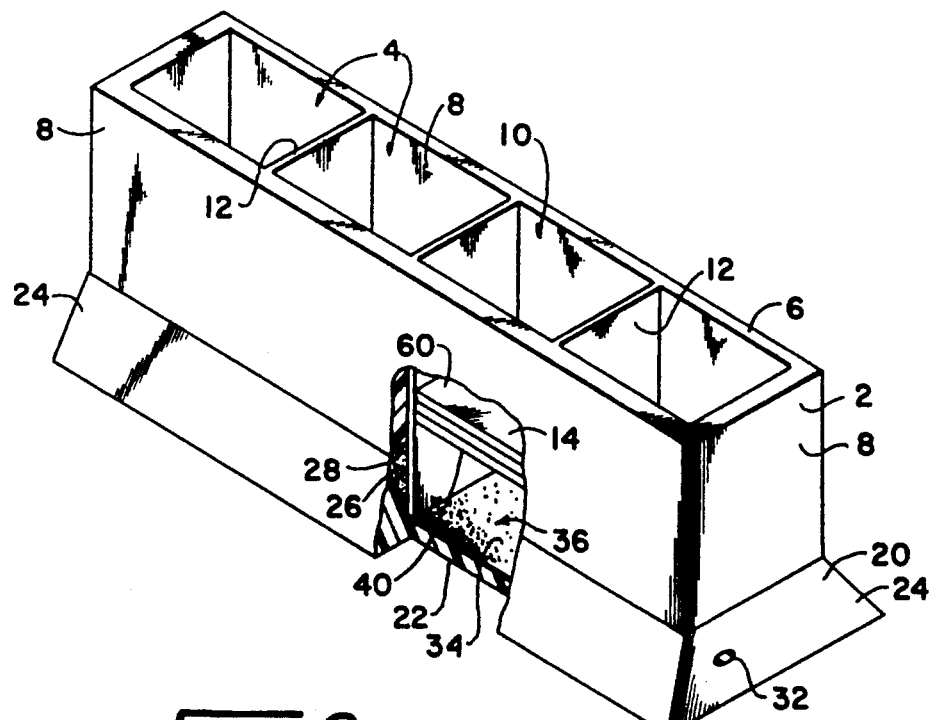
FIG. 2 is a perspective view of the components of FIG. 1, but shows the first and second housing components assembled.

Referring to the drawings, particularly FIGS. 1 and 2, it will be seen that one illustrative embodiment of the invention includes a first housing 2 having a plurality of openings 4 in a top surface 6 thereof. The openings 4 are defined by wall means 8 depending from the top surface 6. The wall means 8 define conduits 10 which extend from the top surface 6 through the first housing 2.

The wall means 8 include barrier walls 12 disposed between each adjoining two of the conduits 10. Assay means 14 are disposed in each of the conduits 10 and are adapted to permit flow of a liquid under test therethrough, as will be further described hereinbelow. The barrier walls 12 extend beyond a bottom plane 16 of the first housing 2, as illustrated in FIG. 1.

The diagnostic device of the present invention further includes a second housing 20, which comprises a reservoir portion, having a bottom wall 22 and upstanding side walls 24. The side walls 24 may be pyramidally configured in cross-section (FIG. 2), such that different sizes of first housings may abut an inclined interior surface portion 26 of the side wall 24. The lower edge 28 of the first housing 2 is fixed to the surface 26 of the second housing side wall 24, as by ultrasonic welding, to form a combined housing. A distal edge 30 of each of the barrier walls 12 extends to a point proximate the bottom wall 22.

The second housing side wall 24 is provided with a port 32 by which pressure is reduced in the second housing, and thereby in the lower regions of the conduits 10, to draw flow of liquid material, after introduction into the conduits 10 through the openings 4, through the conduits and through the assay means 14.

The bottom wall 22 of the second housing 20 is covered, wholly or in part, with a layer of absorbent material 34 before joining of the first and second housings 2,20. Upon joining of the housings 2,20, the distal edges 30 of the barrier walls 12 are disposed adjacent the absorbent material 34. The presence of the absorbent material 34 and the barrier walls 12 greatly reduces the possibility of liquid having passed through one conduit and assay means reaching a neighboring assay means. The absorbent material 34 tends to absorb liquid droppings from an assay means 14 and if, because of the quantity of liquid involved, there is a splash off the bottom wall of the second housing, the barrier walls 12 operate to stop the flight of errant droplets before they reach an adjoining conduit. The first housing barrier walls 12 and the second housing side walls 24 form a reservoir chamber 36 at a lower end of each conduit 10, into which tested liquid drops from the assay means 14. The absorbent material 34 and the barrier walls 12 operate to confine such liquid to its respective chamber 36.

Figure 8:
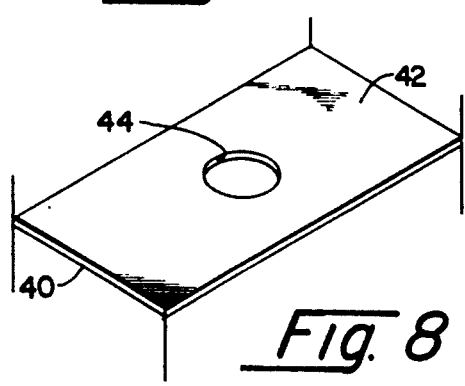
FIG. 8 is a perspective view of a membrane assembly support means.

Each of the conduits 10 is provided with a membrane support means 40, which comprises a substantially planar member 42 having an orifice 44 therethrough (FIG. 8). The member 42 is fixed in place in each of the conduits 10 and may be molded integrally with the conduit wall means 8.

Figure 3:
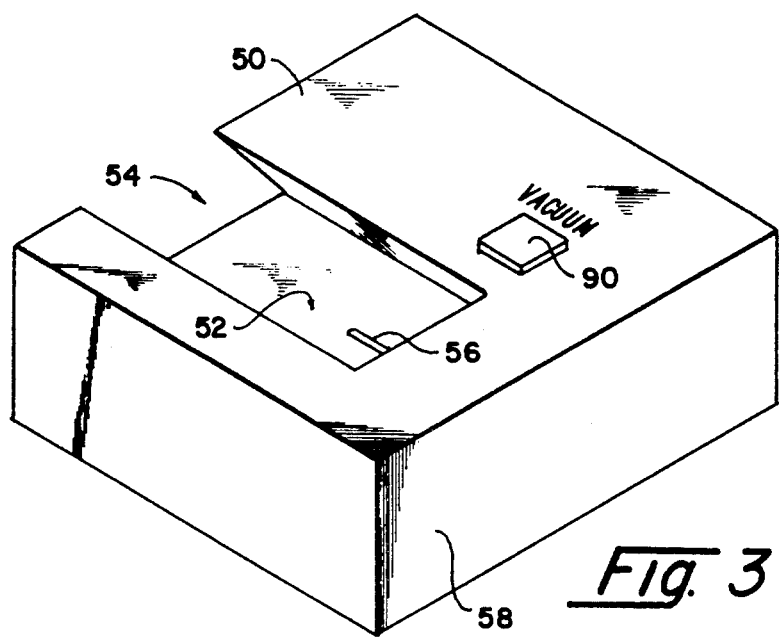
FIG. 3 is a perspective view of one embodiment of a vacuum generating apparatus for use in conjunction with the diagnostic device shown in FIGS. 1 and 2, the diagnostic device and the vacuum generating apparatus together providing a diagnostic assembly illustrative of an alternative embodiment of the invention.

Referring to FIG. 3, there will be seen a vacuum generating apparatus for use in combination with the above-described diagnostic device. The vacuum generating apparatus comprises a housing 50 having a trough 52 therein. In the preferred embodiment illustrated, the trough 52 is open at one end 54 and is adapted to slidingly receive the diagnostic device through the open end. A luer 56, a bayonet-type projection in communication with a vacuum source, extends inwardly of the trough from a wall 58 defining a closed end of the trough. The luer 56 is aligned with the diagnostic device second housing port 32, when the diagnostic device is slid into the trough 52, and is adapted to slidingly enter the port 32 to facilitate generation of a vacuum, or reduced pressure, in the diagnostic device, while leaving exposed the top surface 6 of the diagnostic device to facilitate introduction of liquid into the conduits 10.

To accept and retain the diagnostic device, the trough 52 is shaped complementarily to at least the second housing 20 of the diagnostic device, such that the second housing 20 is easily slid into the trough, with the luer 56 entering the port 32. Alternatively, the trough may be closed at both ends (not shown) and the diagnostic device simply dropped into the trough and then slid into engagement with the luer. The distal edges 30 of the barrier walls 12 only lightly touch, or may be very slightly removed from, the absorbent material 34, such that the barrier walls do not impede establishment of a vacuum throughout the second housing and the lower portions of the first housing.

Figure 4:
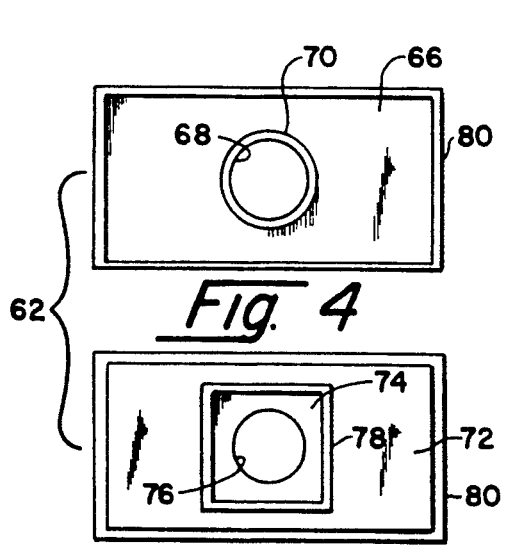
FIG. 4 is a bottom view of a first plate member of a membrane holder assembly.
Figure 5:
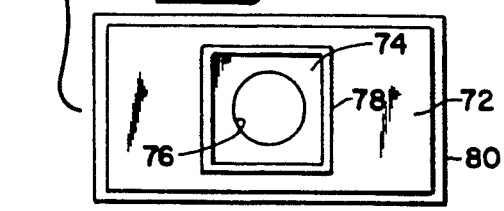
FIG. 5 is a top plan view of a second plate member of the membrane holder assembly.
Figure 6:
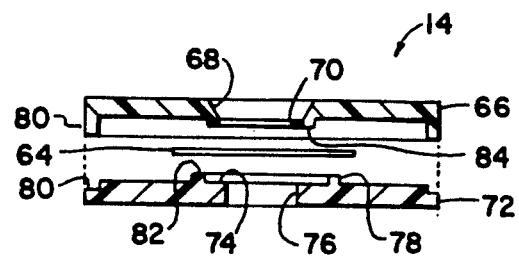
FIG. 6 is a centerline sectional view of the first and second plate members of FIGS. 4 and 5 in position to be joined together with a membrane means therebetween, to form a membrane assembly illustrative of another aspect of the invention.
Figure 7:
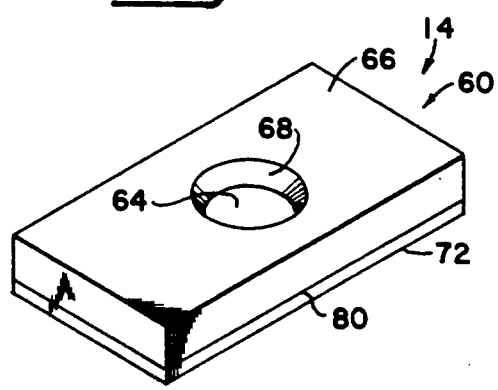
FIG. 7 is a perspective view of an assembled membrane assembly.

The assay means 14 comprises a membrane assembly 60 which includes a membrane holder assembly 62 in combination with a membrane means 64. Referring to FIGS. 4-6, it will be seen that the illustrative membrane holder assembly 62 includes a first plate member 66 having a first orifice 68 therein and a depending retainer wall 70 disposed peripherally of the first orifice 68. The membrane holder assembly 62 further includes a second plate member 72 having a recess 74 therein and a second orifice 76 in the recess 74 and extending through the second plate member 72. The second plate member 72 is provided with an upstanding retainer ridge 78 which forms the recess 74 which receives and retains the membrane means 64.

With the membrane means 64 in place in the recess 74, the first and second plate members 66,72 are locked together by interfitting detent and recess means 80, which may be about their peripheries, as illustrated, or may be a series of projections and recesses, or the like, adapted to "snap" into essentially a permanent lock, with the membrane means disposed between the first and second orifices 68,76. When snapped together, a free edge 82 of the retainer ridge 78 is engaged with an undersurface of the first plate member 66 peripherally of the membrane means 64. Similarly, a free edge 84 of the depending retainer wall 70 is engaged with the membrane means 64 peripherally of the first orifice 68. The retainer wall 70 prevents migration of the liquid passing through the membrane means beyond the wall 70. If, for some reason, there is migration beyond the wall 70, such migration will be stopped at the edge of the membrane means 64 in conjunction with the ridge 78. If, for some reason, there is migration beyond the ridge 78, which is most unlikely, but may result from an accidental spill, the walls 12 segregate one test conduit from another. Thus, the liquid being tested is restricted to a very limited area when passing through the assay means and, thereafter, when entering the reservoir chamber area, substantially eliminating the migration problem.

If desired, membranes of different characteristics may be used in the same device, but in different conduits, for comparison. For example, an operator might elect to use a nylon membrane in one test conduit and a nitrocellulose or cellulose acetate membrane in another conduit; or an operator may elect to use the same, or similar materials, but having different weaves; or may elect to compare results of membranes of different manufacturing sources.

In operation, selected pre-prepared membrane assemblies 60 are placed in the conduits 10. The membrane assemblies are moved into the conduits until the membrane assemblies rest upon the respective membrane support means 40. At this point, the membrane assemblies, through a detent and recess means (not shown) lock into place with an audible "snap" and perceptible "feel" so that the operator may perceive that the membrane assemblies are securely in place.

The diagnostic device is then connected to the vacuum apparatus by way of sliding the diagnostic device second housing 20 into and through the open end 54 of the complementarily shaped trough 52. The housing 20 is slid into abutting engagement with the trough wall 58, in the course of which the luer 56 enters the housing 20 by way of the port 32. A vacuum, or reduced pressure, is generated, typically by simply pushing a vacuum start button 90 on the vacuum apparatus housing 50. Preferably, the housing 50 contains a vacuum pump (not shown) which immediately generates reduced pressure in the diagnostic device second housing 20 and in the first housing 2 below the membrane means 64.

The operator may then introduce a liquid to be tested into one of the conduits 10, The liquid is drawn through the membrane means 64, leaving particulates, in concentrated fashion, on the membrane for reaction with enzymes, or the like, with which the membrane previously has been prepared. The liquid then drops into the reservoir chamber 36 of its conduit 10 and is absorbed by the material 34, preventing its evacuation through the vacuum port 32 and luer 56.

In view of the many safeguards disposed around the individual membrane means and the isolation of the reservoir chambers, along with the absorbent material disposed in the reservoir chamber, there is little likelihood of migration or "cross-talk" from one conduit to another, insuring that no test is run on membrane material contaminated by a previous test.

It is to be understood that the present invention is by no means limited to the particular methods herein disclosed and/or shown in the drawings, but also comprises any modifications or equivalents within the scope of the claims.

Having thus described my invention, what I claim as new and desire to secure by Letters Patent of the United States is:

1. A method of safely assaying, collecting and containing a liquid associated with tests performed on bodily fluids, comprising the steps of:
   a) providing a device comprising a first housing and a second housing integrally formed together, whereby the first housing has a plurality of openings in a top surface thereof, whereby the second housing comprises a reservoir, wherein a plurality of conduits defined by barrier walls and support walls, extend from said plurality of openings, respectively, through the first housing, the support walls being capable of receiving a membrane holder and the barrier walls extending into the second housing for defining a plurality of chambers in the reservoir, such that each of the conduits respectively, is in fluid communication with a chamber corresponding thereto, such that each of the plurality of chambers contains and confines a liquid from an assay performed in its corresponding conduit, each of the chambers preventing cross contamination with other of the plurality of chambers, each of the plurality of chambers being inseparable from its corresponding conduit,
   b) placing an assay membrane onto a membrane holder formed by locking a first plate with a second plate, whereby the assay membrane lies between the first plate and the second plate,
   c) placing the membrane holder with the assay membrane thereon, onto a support wall in one of the plurality of conduits in the first housing,
   d) passing a liquid from the bodily fluid to be assayed through the assay membrane in the conduit, wherein a reduced pressure only, is applied to the liquid passing through the assay membrane, thereby causing particulate matter contained in the liquid to remain on the assay membrane,
   e) performing an assay on the particulate matter remaining on the assay membrane,
   f) repeating steps b) through e) until as many conduits as desired have been contaminated by performing an assay therein and each corresponding chamber is filled with a liquid safely contained therein.

2. The method of claim 1 wherein step f) further comprises selecting an assay membrane comprising a material, wherein the material of the assay membrane differs from the material of at least one other assay membrane in at least one of the plurality of conduits in which an assay has been performed.

3. The method of claim 1 wherein step a) further comprises providing an absorbent member in said reservoir, wherein said absorbent member is divided by the barrier walls.

* * * * *